US007026166B2

(12) United States Patent
Suich et al.

(10) Patent No.: US 7,026,166 B2
(45) Date of Patent: Apr. 11, 2006

(54) FLUOROGENIC DYES

(75) Inventors: Daniel J. Suich, Oakland, CA (US); Ronald N. Zuckermann, El Cerrito, CA (US)

(73) Assignee: Chiron Corporation, Emeryville, CA (US)

( * ) Notice: Subject to any disclaimer, the term of this patent is extended or adjusted under 35 U.S.C. 154(b) by 170 days.

(21) Appl. No.: 10/349,256

(22) Filed: Jan. 21, 2003

(65) Prior Publication Data

US 2003/0165955 A1   Sep. 4, 2003

Related U.S. Application Data

(60) Provisional application No. 60/351,168, filed on Jan. 22, 2002.

(51) Int. Cl.
G01N 21/76 (2006.01)

(52) U.S. Cl. ...................... 436/172; 436/528; 436/529; 436/531; 436/532; 436/533; 436/534; 436/537; 436/546; 436/63; 436/91; 436/111; 436/112; 436/119; 436/120; 436/126; 436/129; 436/800; 435/7.1; 435/7.6; 435/7.8; 435/459; 435/177; 435/178; 435/180; 435/181; 435/188; 435/961; 435/DIG. 1; 435/DIG. 2; 435/DIG. 14; 435/DIG. 16; 435/DIG. 17; 435/DIG. 18; 424/9.6; 424/707; 424/278.1

(58) Field of Classification Search ................ 435/7.2, 435/7.21, 7.23, 7.24, 7.8, 29, 455–490, 7.1, 435/7.6, 459, 177, 178, 180, 181, 188, 961, DIG. 1, DIG. 2, DIG. 14, DIG. 16, DIG. 17, DIG. 18; 436/56, 800, 164, 172, 528, 529, 531, 532, 533, 534, 537, 546, 63, 91, 111, 112, 119, 120, 126, 129; 424/9.6, 707, 278.1; 549/223, 225, 227

See application file for complete search history.

(56) References Cited

U.S. PATENT DOCUMENTS 3,728,113 A * 4/1973 Becker et al. .............. 430/223
3,854,945 A * 12/1974 Bush et al. ................. 430/224

(Continued)

FOREIGN PATENT DOCUMENTS

DE    199 35 302 A1 * 2/2001

(Continued)

OTHER PUBLICATIONS

Daugherty PS et al. Flow cytometric screening of cell-based libraries. J. Immunol. Methods 2000;243:211-227.*

(Continued)

Primary Examiner—Long V. Le
Assistant Examiner—David J. Venci
(74) Attorney, Agent, or Firm—James E. Austin; Young J. Suh; Alisa A. Harbin

(57) ABSTRACT

The present invention relates to the use of fluorogenic or chromogenic dyes as reporter molecules for detecting cell entry by a specific molecule.

19 Claims, 3 Drawing Sheets

U.S. PATENT DOCUMENTS

| | | | |
|---|---|---|---|
| 4,713,324 A * | 12/1987 | Fox et al. .................. | 435/4 |
| 4,751,286 A * | 6/1988 | Packard et al. ............ | 530/391.5 |
| 4,868,132 A * | 9/1989 | Byrnes et al. .............. | 436/546 |
| 4,889,916 A * | 12/1989 | Packard et al. ............ | 525/54.1 |
| 5,055,561 A * | 10/1991 | Packard et al. ............ | 530/391.5 |
| 5,573,773 A * | 11/1996 | Kis et al. ................... | 424/423 |
| 5,573,904 A | 11/1996 | Mattingly | |
| 5,756,771 A * | 5/1998 | Mattingly .................. | 549/223 |
| 5,800,996 A * | 9/1998 | Lee et al. ................... | 435/6 |
| 5,804,604 A | 9/1998 | Frank et al. | |
| 5,986,094 A | 11/1999 | Ghoshal et al. | |
| 6,221,604 B1 | 4/2001 | Upadhya et al. | |
| 6,379,965 B1 * | 4/2002 | Boutin ....................... | 435/455 |
| 6,756,207 B1 * | 6/2004 | Giuliano et al. ............ | 435/7.2 |
| 2002/0151062 A1 * | 10/2002 | Zuckermann et al. ....... | 435/455 |
| 2003/0215798 A1 * | 11/2003 | Short et al. ................. | 435/6 |

FOREIGN PATENT DOCUMENTS

| | | |
|---|---|---|
| EP | 0264797 | 1/1996 |
| WO | WO 79/00515 | 8/1979 |
| WO | WO 94/04686 | 3/1994 |
| WO | WO 98/52614 | 11/1998 |
| WO | WO 01/08707 A2 * | 2/2001 |

OTHER PUBLICATIONS

Huang CY et al. Lipitoids—novel cationic lipids for cellular delivery of plasmid DNA in vitro. Chemistry & Biology 1998;5:345-354.*

Wender PA et al. The design, synthesis, and evaluation of molecules that enable or enhance cellular uptake: Peptoid molecular transporters. Proc. Natl. Acad. Sci. USA. 2000; 97:13003-13008.*

Murphy JE et al. A combinatorial approach to the discovery of efficient cationic peptoid reagents for gene delivery. Proc. Natl. Acad. Scid. USA. 1998;95:1517-1522.*

Corrie, J.E.T. et al. A homobifunctional rhodamine for labeling proteins with defined orientations of a fluorophore. Bioconjugate Chem. 1998;9:160-167.*

Forkey, J.N. et al. Protein structural dynamics by single-molecule fluorescence polarization (Review). Prog. Biophys. Mol. Biol. 2000;74:1-35.*

Wingender, E. & Arellano, A. Synthesis and properties of the thiol-specific reagent difluorescein disulfide: its application on histon-histone and histone-DNA interactions. Anal. Biochem. 1982;127:351-360.*

Graber et al., "Characteristics of Fluorprobes for Measuring Intracellular pH", Analytical Biochemistry 156, 202-212 (1986).

Shipchandler et al., "4'-[Aminomethyl] fluorescein and Its N-Alkyl Derivatives: Useful Reagents in Immunodiagnostic Techniques", Analytical Biochemistry 162, 89-101 (1987).

Rothbard et al., Conjugation of arginine oligomers to cyclosporin A facilitates topical delivery and inflammation, Nature Medicine, vol. 6, No. 11, Nov. 2000, pp. 1253-1257.

Dive et al., "Polar fluorescein derivatives as improved substrate probes for flow cytoenzymological assay of cellular esterases", Molecular and Cellular Probes (1988) 2, 131-145.

Fawell et al., "Tat-mediated delivery of heterologous proteins into cells", Proc. Natl. Acad. Sci USA, vol. 91, Jan. 1994, pp. 664-668.

* cited by examiner

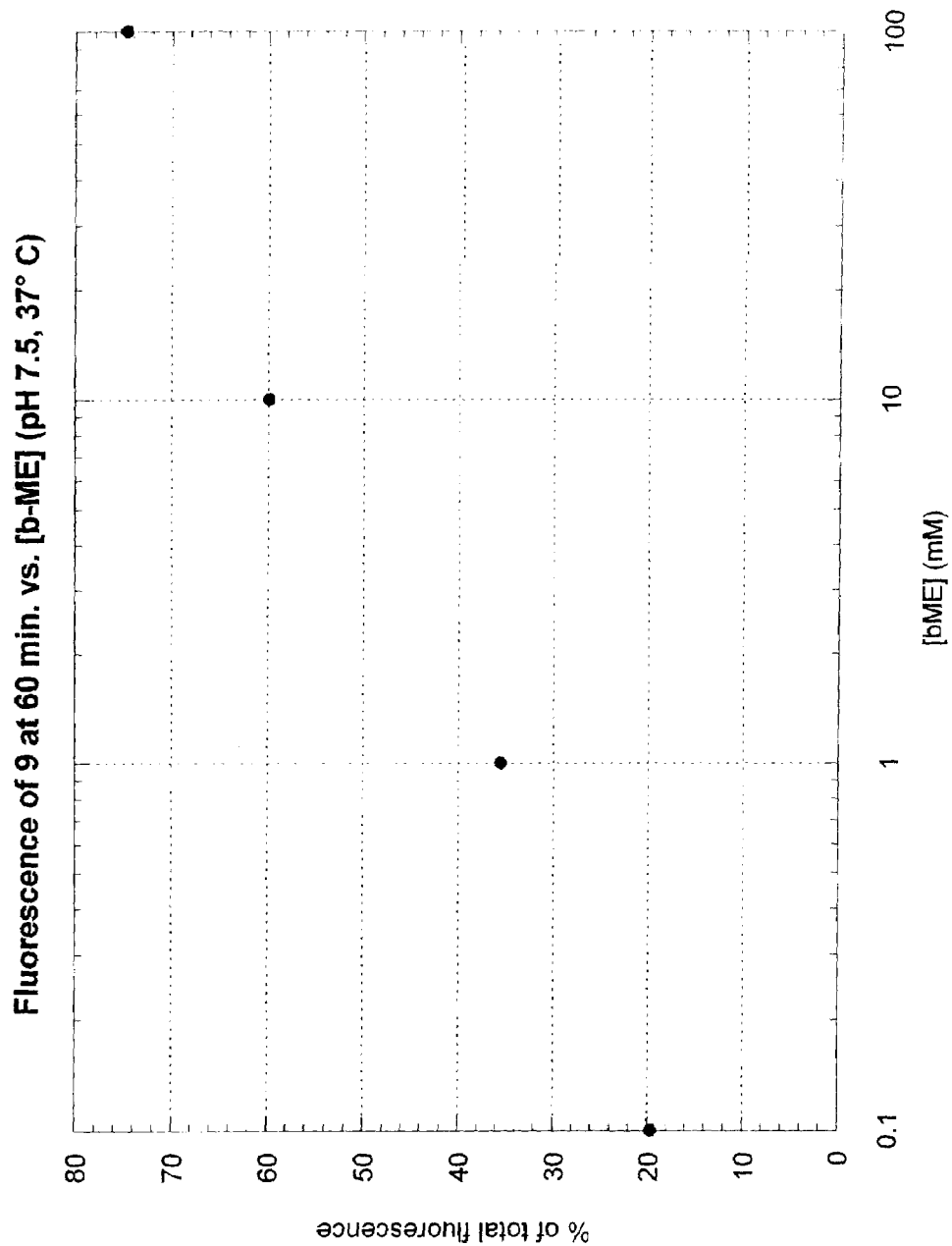

FLUOROGENIC DYES

This application claims the benefit of U.S. provisional application 60/351,168, filed Jan. 22, 2002.

1 BACKGROUND OF THE INVENTION

1.1 Field of the Invention

The present invention relates to the use of fluorogenic or chromogenic dyes as reporter molecules for detecting cell entry by a specific molecule. The present invention has application to cellular assays, including high throughput assays that utilize fluorogenic or chromogenic reporters to detect transportation of a molecule across a cell membrane.

1.2 The Related Art

Numerous fluorescent and fluorogenic dyes have been used as reporters in fluorodetection assays. In particular, numerous fluorescein derivatives have been reported which possess functional groups that are suitable for reacting with other molecules and have been used as tracers in analytical applications ranging from the probing of cell functions to the monitoring of the level of one or more drugs in physiological test samples. See, e.g., C. Dive, et al., *Mol. Cell. Probes* 2:31 (1988); Graber, et al., *Anal. Biochem.* 156:202 (1986); P. J. Brynes, et al., U.S. Pat. No. 4,869,132 and N. Y. Wang, et al., EP 264797. Examples of analytical applications wherein such compounds are used include by way of example fluorescent polarization immunoassays (FPIAs) for use in commercially available instruments such as the Abbott $AD_x$ and Abbott $TD_x$ instruments (both available from Abbott Labs, Abbott Park, Ill.). Examples of such derivatives include 5- and 6-amino fluorescein (M. T. Ship Chandler, et al., *Anal. Biochem.* 162:89 (1987); Mattingly, U.S. Pat. No. 5,573,904 (1996) and U.S. Pat. No. 5,756,771 (1996), and Ghoshal, et al, U.S. Pat. No. 5,986,094 (1999)).

Fluorescein dyes particularly have been used to detect cell entry. For example, fluorescein 1 has been employed especially to detect cell entry by peptides. Additionally, carboxy-fluorescein diacetate 2 and its derivatives find known application in staining liver cells because upon entry a cellular esterase cleaves the ester moiety resulting in the generation of fluorescein, which is highly fluorescent. Monobromobimane 3, which does not fluoresce until reacted with a thiol, has also been used to detect cell entry. In particular, this compound does not fluoresce until it contacts the cell cytoplasm and interacts with glutathione, a tripeptide thiol. Thus, 3 can be used to detect cell entry or intracellular thiol levels based on an increase in fluorescence relative to the extracellular environment, which typically contains little or no free thiol. Further, electron-deficient heterocycle-substituted fluorescent dyes have been used as fluorimetric reporter molecules (see, e.g., U.S. Pat. No. 6,221,604).

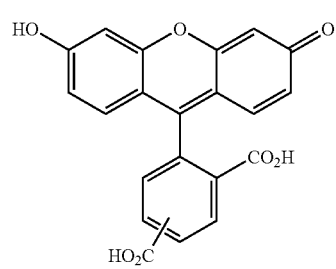

1

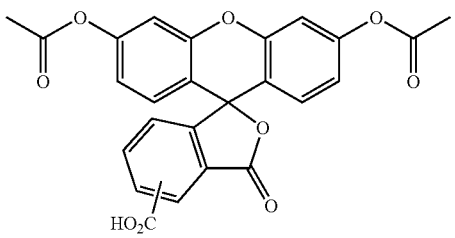

2

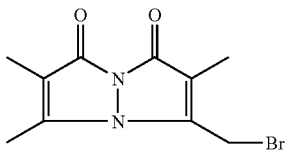

3

However, while fluorescein derivatives have been widely used as reporter molecules to detect cell entry, known fluorescein derivatives suffer from significant disadvantages. For example, the use of known fluorescein dyes to detect cell entry requires tedious separation of intracellular fluorescence from extracellular fluorescence; and, therefore, the use of fluorescein dyes to detect cell entry are not amenable to high-throughput assays. Moreover, carboxy-fluorescein diacetate 1 suffers from a short half-life, which has been attributed to the hydrolysis of its ester moieties at physiological pH.

Certain peptides are recognized to possess the ability to enter cells as well as to transport attached molecules into cells. Examples of such peptides include those derived from HIV tat protein, lysine polymers, Antennapedia homeodomain, and Arg 9 among others. (See e.g., U.S. Pat. No. 5,804,604 by Frank, et al., relating to the use of HIV tat protein derivatives to facilitate intracellular delivery of cargo molecules; WO 98/52614, which discloses the use of arginine polymers containing guanidino or amidino side chains to facilitate cell entry; WO 79/00515, which discloses the use of high molecular weight lysine polymers to facilitate cell entry of target molecules; and WO 94/04686 (1984) and Fawell, et al., *Proc. Natl. Acad, Sci., USA* 91:664–668 (1994), each of which discloses the use of peptides derived from HIV tat to promote the transport of molecules across cell membranes). Also, certain peptoid sequences have been demonstrated to facilitate intracellular transport (Wender, et al., *Proc. Natl. Acad. Sci., USA* 97:13003–13008 (2000)). Arginine oligomers have also been reported to deliver topically a cyclic peptide drug, cyclosporin A, into cells to inhibit inflammation (Rothbard, et al., *Nature Med.* 6:1253–7 (2000)).

Physicochemical methods to facilitate the delivery of macromolecules into cells have been developed. Such methods include, by way of example, electroporation, membrane fusion with liposomes, calcium-phosphate-DNA precipitation, DEAE-dextran-mediated transfection, infection with modified nucleic acids and direct microinjection into cells.

However, despite foregoing descriptions of fluorogenic compounds and carrier molecules, the identification of new fluorogenic molecules that are effectively transported into cells and more efficient methods for identifying such molecules would be beneficial.

2 SUMMARY OF THE INVENTION

The present invention provides novel fluorogenic compounds and associated compositions and methods including such compounds. The compounds, compositions, and methods provided by the invention are useful in applications requiring quantitative detection of cellular uptake of compounds.

Thus, in one aspect, the present invention provides novel fluorogenic compounds that produce a detectable signal upon uptake by a cell. In one embodiment, the novel compounds provided by the invention have the structure shown below (4):

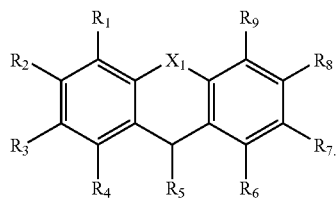

The substituent $R_5$ is a spirocyclic moiety having the formula:

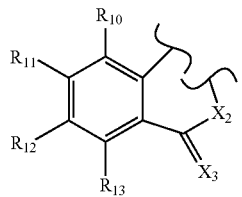

wherein the phenyl ring of $R_5$ can be oriented above or below the face of the plane defined by the fused ring system of compound 4. $R_2$ and $R_8$ independently have the structure:

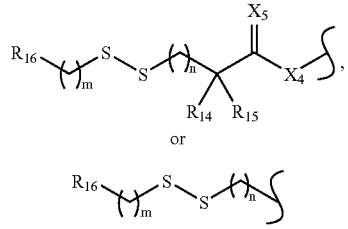

where the indices m and n independently are integers between 0 and 5 inclusive, such that the sum m+n is equal to or less than ten. $R_1$, $R_3$, $R_4$, $R_6$, $R_7$, and $R_9$–$R_{16}$ are selected independently from the group consisting of hydrogen, halo, cyano, amino, azido, aldehyde, mercapto, hydroxy, nitro, and optionally substituted, alkyl, cycloalkyl, alkenyl, alkynyl, aryl, acyl, mono- or di- or trialkylammonium, guanidino, carboxamido, carboxy, methylamino, haloacetamido, hydrazido, maleimido, keto, oxime, (mono-, di-, tri-)halomethyl, hydroxamic acid, hydroxylamino, alkoxy, sulfate, sulfonate, phosphate, phosphonate, sulfonyl, sulfonamide, isothiocyanate, halosulfonyl, carboxyazido, semicarbazido, thiosemicarbazido, sulfonylhydrazido, carbodimide. $X_1$–$X_5$ independently can be oxygen, sulfur, or $NR_{17}$, where $R_{17}$ is hydrogen or optionally substituted lower alkyl. The indices m and n independently are integers between 0 and 20 inclusive.

In some embodiments, m and n are selected independently from integers between 1 and 3 inclusive. In more particular embodiments, m and n are selected independently from integers between 1 and 3 inclusive, and $R_3$–$R_6$ are selected independently from hydrogen, alkyl, cycloalkyl. In still more particular embodiments, In still more particular embodiments, m and n are selected independently from integers between 1 and 3 inclusive, and $R_3$–$R_6$ are selected independently from hydrogen, alkyl, cycloalkyl; and $X_1$–$X_7$ are each oxygen.

In still another aspect, the invention to provide improved methods for identifying molecules capable of entering cells and, more particularly, molecules useful to facilitate the entry of other molecules into cells, such as, for example, a fluorogenic or chromogenic dyes, which dyes optionally may be attached to another compound such as a therapeutic. In some embodiments, the methods for identification of molecules comprise high-throughput assays to detect cell entry. In other embodiments, the molecules to be identified are peptoids. In more particular embodiments, the peptoids are conjugated with a fluorogenic or chromogenic compound, such as carboxyfluorescein diacetate ("CFDA"), bis(pivaloyl)carboxyfluorescein, monobromobimane, di-β-D-galactopyranoside ("FDG"), or a compound of the invention, so that cellular uptake of the peptoid can be determined efficiently. In other specific embodiments, the present invention includes methods that comprise screening combinatorial peptoid libraries to identify peptoids that cross the cell membrane and/or peptoids that function to facilitate molecular transport, in which the peptoids being screened are attached covalently to a fluorogenic or chromogenic reporter molecule, and determining whether the resulting conjugate produces increased fluorescence when contacted with a cell. The peptoids can be conjugated with a fluorogenic or chromogenic compound, such as carboxyfluorescein diacetate ("CFDA"), bis(pivaloyl)carboxyfluorescein, monobromobimane, or di-β-D-galactopyranoside ("FDG"), or a compound of the invention.

These and other aspects and advantages will become apparent when the Description below is read in conjunction with the accompanying Drawings.

3 BRIEF DESCRIPTION OF THE DRAWINGS

Figure 1:
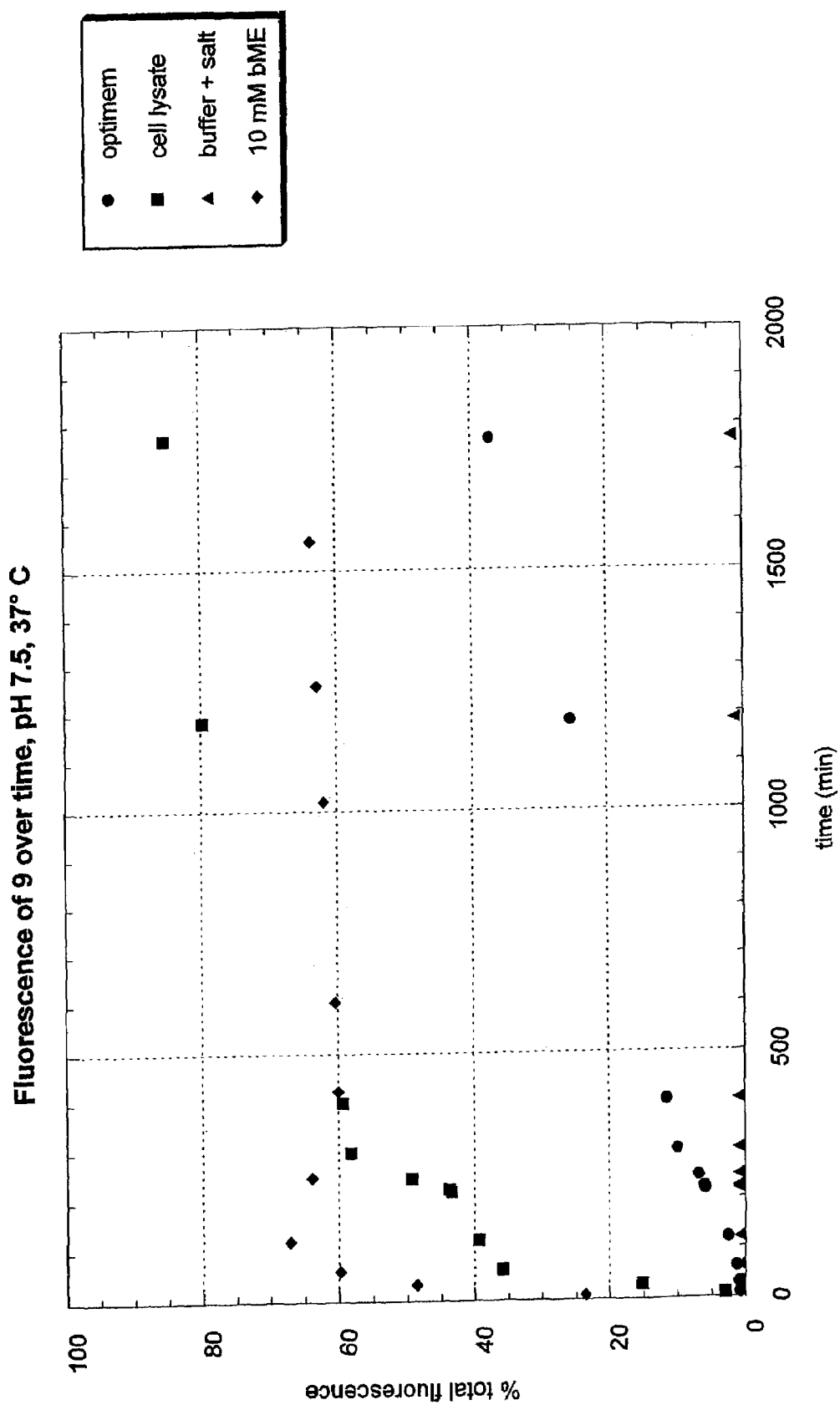
FIG. 1 shows the fluorescence of bis(4-(2'-(trimethylamino)ethanedithio)-2,2-dimethylbutyryl)carboxyfluorescein (compound 9, see Section 5.5) over time at pH 7.5 and 37° C. in a HeLa cell-based assay.

FIG. 3 shows the fluorescence of compound 9 after 60 minutes in the presence of β-mercaptoethanol ("β-ME") at pH 7.5, 37° C. at concentrations of 0.1, 1, 10 and 100 mM β-ME.

4 DESCRIPTION OF SOME EMBODIMENTS OF THE INVENTION

4.1 Definitions

4.1.1 Peptoid

A "peptoid" is a poly(N-substituted amide), preferably a poly(N-substituted glycine), as known in the chemistry and bioorganic chemistry arts and described, for example, in co-owned PCT Publications WO 94/06451, WO 98/06437, WO 99/08711, and U.S. Pat. Nos. 5,877,278; 6,251,433; 6,197,332; 6,075,121; 5,977,301; 5,965,695; 5,877,278; and 5,831,005 each of which is incorporated herein by reference in its entirety and for all purposes. In some embodiments of the invention, the peptoids have the structure shown below:

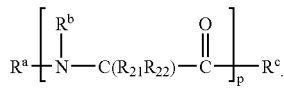

$R^a$ and $R^c$ are selected independently from the group consisting of alkyl, aryl, aralkyl, aralkenyl, and aralkynyl, any of which may be substituted. In some embodiments, $R^a$ and/or $R^c$ is substituted with a lipid moiety, wherein the lipid moiety may be conjugated to a linker moiety. $R^b$ is independently selected from the group consisting of alkyl, aryl, aralkyl, aralkenyl, and aralkynyl, any of which may be substituted. $R_{21}$, and $R_{22}$ are independently selected from hydrogen, and optionally substituted lower alkyl and lower alkoxy. The index p is an integer selected from 2 to about 50, more specifically between about 4 and about 30, still more specifically between about 6 and about 20, and yet more specifically between about 8 and about 15. As used herein, the term "peptoid" encompasses lipitoids and cholesteroids, which are described in Section 4.1.3 and in co-owned U.S. Pat. Nos. 6,251,433 and 6,197,332; and PCT Publication. Nos. WO 99/08711 and WO 98/06437, each of which is incorporated herein by reference in its entirety and for all purposes.

4.1.2 Lipid Moiety

A "lipid moiety" is a hydrophobic moiety having a substantial hydrocarbon component, preferably comprising a group selected from $C_{10}$–$C_{50}$ branched or unbranched alkyl, alkenyl or alkynyl, $C_{14}$–$C_{50}$ aryl, aralkyl, aralkenyl, or aralkynyl, or a steroid nucleus. Examples of lipid moieties include dialkyl- or dialkenyl-phospholipids, such as phosphatidylcholines, phosphatidylethanolamines and phosphatidylinositols, glycolipids, such as cerebrosides and gangliosides, fatty diacylglycerides, glycosylglycerides, sphingolipids, and steroids, including sterols.

4.1.3 Lipitoid

A "lipitoid" is a lipid-substituted peptoid, i.e., a compound described in Section 4.1.1 where $R^a$ comprises a lipid moiety. A "cholesteroid" is a cholesterol-substituted peptoid, i.e., a compound described in Section 4.1.1 where $R^a$ comprises a cholesteryl moiety. While cholesterols are preferred in some applications, further disclosure of steroids useful for incorporating into steroid-peptoid conjugates is found in PCT publication WO 97/46223 (Fasbender et al.) and corresponding U.S. Pat. No. 5,935,936, which are hereby incorporated by reference.

4.1.4 Alkyl, Alkenyl, Alkynyl

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Alkenyl" refers to an acyclic monovalent radical containing carbon and hydrogen, which may be branched or a straight chain, and which contains at least one carbon-carbon double bond. The alkenyl group may be monounsaturated or polyunsaturated. Similarly, "alkynyl" refers to such a radical having at least one carbon-carbon triple bond. "Lower" alkyl (alkenyl, alkynyl, alkoxy, etc.) refers to a group having 1 to 6 carbons, preferably 1 to 4 carbons. An alkyl, alkenyl, or alkynyl group can be optionally substituted; in some embodiments, the substituent is selected from the group consisting of halogen, lower alkyl, lower alkoxy, nitro, amide, tertiary amino, hydroxy, and haloloweralkyl.

4.1.5 Aryl

"Aryl" refers to a substituted or unsubstituted monovalent aromatic radical having a single ring (e.g., benzene) or two or three condensed rings e.g., naphthyl or phenanthryl). Groups having a single ring (monocyclic) or two condensed rings (bicyclic) are generally preferred, with monocyclic groups being particularly preferred. The term includes heteroaryl groups, which are aromatic ring groups having one or more nitrogen, oxygen, or sulfur atoms in the ring, such as furan, pyrrole, pyridine, imidazole, and indole. By "substituted" is meant that one or more ring hydrogen atoms in the aryl group is replaced with a non-hydrogen group, preferably selected from halogen, lower alkyl, lower alkoxy, nitro, amide, tertiary amino, hydroxy, and halo(lower alkyl).

4.2 Fluorogenic Compounds

In one aspect, the present invention provides novel fluorogenic compounds having the have the structure shown below (4):

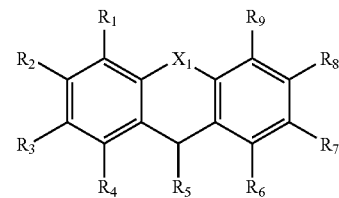

The substituent $R_5$ is a spirocyclic moiety having the formula:

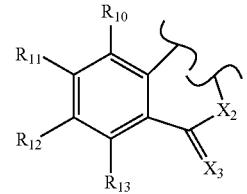

wherein the phenyl ring of $R_5$ can be oriented above or below the face of the plane defined by the fused ring system of compound 4. $R_2$ and $R_8$ independently have the structure:

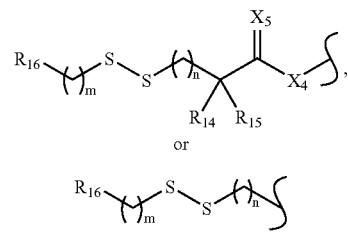

where the indices m and n independently are integers between 0 and 5 inclusive, such that the sum m+n is equal to or less than ten. $R_1$, $R_3$, $R_4$, $R_6$, $R_7$, and $R_9$–$R_{16}$ are selected independently from the group consisting of hydrogen, halo, cyano, amino, azido, aldehyde, mercapto, hydroxy, nitro, and optionally substituted, alkyl, cycloalkyl, alkenyl, alkynyl, aryl, acyl, mono- or di- or trialkylammonium, guanidino, carboxamido, carboxy, methylamino, haloacetamido, hydrazido, maleimido, keto, oxime, (mono-, di-, tri-)halomethyl, hydroxamic acid, hydroxylamino, alkoxy, sulfate, sulfonate, phosphate, phosphonate, sulfonyl, sulfonamide, isothiocyanate, halosulfonyl, carboxyazido, semicarbazido, thiosemicarbazido, sulfonylhydrazido, carbodimide. $X_1$–$X_5$ independently can be oxygen, sulfur, or $NR_{17}$, where $R_{17}$ is hydrogen or optionally substituted lower alkyl.

In some embodiments, $X_1$ is oxygen. In more particular embodiments, $X_1$–$X_3$ are oxygen. In still more particular embodiments, $X_1$–$X_5$ are oxygen. Among those embodiments in which $X_1$–$X_5$ are oxygen, more specific embodiments include those in which m is 2, and n is 3. The invention further includes embodiments in which $X_1$–$X_5$ are oxygen, m is 2, n is 3, and $R_{16}$ is trialkylammonium. In more specific embodiments $X_1$–$X_5$ are oxygen, m is 2, n is 3, $R_{16}$ is trialkylammonium, and $R_{14}$ and $R_{15}$ are optionally substituted lower alkyl. Still more specific embodiment are those in which $X_1$–$X_5$ are oxygen, m is 2, n is 3, $R_{16}$ is trialkylammonium, and $R_{14}$ and $R_{15}$ independently are methyl or ethyl. Other more specific embodiments include those in which $X_1$–$X_5$ are oxygen, m is 2, n is 3, $R_{16}$ is trialkylammonium, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_5$ are oxygen, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_5$ are oxygen, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_5$ are oxygen, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In yet other embodiments in which $X_1$–$X_5$ are oxygen m is 2, and n is 3, $R_{16}$ is dialkylamino. In more specific embodiments $X_1$–$X_5$ are oxygen, m is 2, n is 3, $R_{16}$ is dialkylamino, and $R_{14}$ and $R_{15}$ are optionally substituted lower alkyl. Still more specific embodiment are those in which $X_1$–$X_5$ are oxygen, m is 2, n is 3, $R_{16}$ is dialkylamino, and $R_{14}$ and $R_{15}$ independently are methyl or ethyl. Other more specific embodiments include those in which $X_1$–$X_5$ are oxygen, m is 2, n is 3, $R_{16}$ is dialkylamino, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_5$ are oxygen, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_5$ are oxygen, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_5$ are oxygen, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In other embodiments, $X_1$–$X_5$ are oxygen m is 2, and n is 0. The invention further includes embodiments in which $X_1$–$X_5$ are oxygen, m is 2, n is 3, and $R_{16}$ is trialkylammonium. In more specific embodiments $X_1$–$X_5$ are oxygen, m is 2, n is 0, $R_{16}$ is trialkylammonium, and $R_{14}$ and $R_{15}$ are optionally substituted lower alkyl. Still more specific embodiment are those in which $X_1$–$X_5$ are oxygen, m is 2, n is 0, $R_{16}$ is trialkylammonium, and $R_{14}$ and $R_{15}$ independently are methyl or ethyl. Other more specific embodiments include those in which $X_1$–$X_5$ are oxygen, m is 2, n is 0, $R_{16}$ is trialkylammonium, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_5$ are oxygen, m is 2, n is 0, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_5$ are oxygen, m is 2, n is 0, $R_{16}$ is trimethylamnmonium, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_5$ are oxygen, m is 2, n is 0, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In yet other embodiments in which $X_1$–$X_5$ are oxygen m is 2, n is 0, and $R_{16}$ is dialkylamino. In more specific embodiments $X_1$–$X_5$ are oxygen, m is 2, n is 0, $R_{16}$ is dialkylamino, and $R_{14}$ and $R_{15}$ are optionally substituted lower alkyl. Still more specific embodiment are those in which $X_1$–$X_5$ are oxygen, m is 2, n is 0, $R_{16}$ is dialkylamino, and $R_{14}$ and $R_{15}$ independently are methyl or ethyl. Other more specific embodiments include those in which $X_1$–$X_5$ are oxygen, m is 2, n is 0, $R_{16}$ is dialkylamino, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_5$ are oxygen, m is 2, n is 0, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_5$ are oxygen, m is 2, n is 0, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_5$ are oxygen, m is 2, n is 0, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In other embodiments, $X_1$–$X_3$ and $X_5$ are oxygen and $X_4$ is $NR_{17}$. Among those embodiments, more specific embodiments include those in which m is 2, and n is 3. The invention further includes embodiments in which $X_1$–$X_3$ and $X_5$ are oxygen and $X_4$ is $NR_{17}$, m is 2, n is 3, and $R_{16}$ is tnalkylammonium. In more specific embodiments $X_1$–$X_3$ and $X_5$ are oxygen and $X_4$ is $NR_{17}$, m is 2, n is 3, $R_{16}$ is trialkylammonium, and $R_{14}$ and $R_{15}$ are optionally substituted lower alkyl. Still more specific embodiment are those in which $X_1$–$X_3$ and $X_5$ are oxygen and $X_4$ is $NR_{17}$, m is 2, n is 3, $R_{16}$ is trialkylammonium, and $R_{14}$ and $R_{15}$ independently are methyl or ethyl. Other more specific embodiments include those in which $X_1$–$X_3$ and $X_5$ are oxygen and $X_4$ is $NR_{17}$, m is 2, n is 3, $R_{16}$ is trialkylammonium, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_3$ and $X_5$ are oxygen and $X_4$ is $NR_{17}$, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_3$ and $X_5$ are oxygen and $X_4$ is $NR_{17}$, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_3$ and $X_5$ are oxygen and $X_4$ is $NR_{17}$, m is 2, n is 3, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In yet other embodiments in which $X_1$–$X_3$ and $X_5$ are oxygen and $X_4$ is $NR_{17}$, m is 2, and n is 3, $R_{16}$ is dialkylamino. In more specific embodiments $X_1$–$X_3$ and $X_5$ are oxygen and $X_4$ is $NR_{17}$, m is 2, n is 3, $R_{16}$ is dialkylamino, and $R_{14}$ and $R_{15}$ are optionally substituted lower alkyl. Still more specific embodiment are those in which $X_1$–$X_3$ and $X_5$ are oxygen and $X_4$ is $NR_{17}$, m is 2, n is 3, $R_{16}$ is dialkylamino, and $R_{14}$ and $R_{15}$ independently are methyl or ethyl. Other more specific embodiments include those in which $X_1$–$X_3$ and $X_5$ are oxygen and $X_4$ is $NR_{17}$, m is 2, n is 3, $R_{16}$ is dialkylamino, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_3$ and $X_5$ are oxygen and $X_4$ is $NR_{17}$, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_3$ and $X_5$ are oxygen and $X_4$ is $NR_{17}$, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_3$ and $X_5$ are oxygen and $X_4$ is $NR_{17}$, m is 2, n is 3, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In other embodiments, $X_1$–$X_3$ and $X_5$ are oxygen and $X_4$ is $NR_{17}$, m is 2, and n is 0. The invention further includes embodiments in which $X_1$–$X_3$ and $X_5$ are oxygen and $X_4$ is $NR_{17}$, m is 2, n is 3, and $R_{16}$ is trialkylammonium. In more specific embodiments $X_1$–$X_3$ and $X_5$ are oxygen and $X_4$ is $NR_{17}$, m is 2, n is 0, $R_{16}$ is trialkylammonium, and $R_{14}$ and $R_{15}$ are optionally substituted lower alkyl. Still more specific embodiment are those in which $X_1$–$X_3$ and $X_5$ are oxygen and $X_4$ is $NR_{17}$, m is 2, n is 0, $R_{16}$ is trialkylammonium, and $R_{14}$ and $R_{15}$ independently are methyl or ethyl. Other more specific embodiments include those in which $X_1$–$X_3$ and $X_5$ are oxygen and $X_4$ is $NR_{17}$, m is 2, n is 0, $R_{16}$ is trialkylammonium, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_3$ and $X_5$ are oxygen and $X_4$ is $NR_{17}$, m is 2, n is 0, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_3$ and $X_5$ are oxygen and $X_4$ is $NR_{17}$, m is 2, n is 0, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_3$ and $X_5$ are oxygen and $X_4$ is $NR_{17}$, m is 2, n is 0, $R_{16}$ is trimethylammonium, $R_{14}$ and $R_{15}$ independently are methyl or ethyl, and $R_3$, $R_4$, $R_6$, $R_7$, and $R_{10}$–$R_{13}$ are hydrogen or carboxyl, and at least one of $R_{10}$–$R_{13}$ is carboxyl.

In yet other embodiments in which $X_1$–$X_3$ and $X_5$ are oxygen and $X_4$ is $NR_{17}$, m is 2, n is 0, and $R_{16}$ is dialkylamino. In more specific embodiments $X_1$–$X_3$ and $X_5$ are oxygen and $X_4$ is $NR_{17}$, m is 2, n is 0, $R_{16}$ is dialkylamino, and $R_{14}$ and $R_{15}$ are optionally substituted lower alkyl. Still more specific embodiment are those in which $X_1$–$X_3$ and $X_5$ are oxygen and $X_4$ is $NR_{17}$, m is 2, n is 0, $R_{16}$ is dialkylamino, and $R_{14}$ and $R_{15}$ independently are methyl or ethyl. Other more specific embodiments include those in which $X_1$–$X_3$ and $X_5$ are oxygen and $X_4$ is $NR_{17}$, m is 2, n is 0, $R_{16}$ is dialkylamino, $R_{14}$ and $R_{15}$ independently are methyl or ethyl, and $R_3$, $R_4$, $R_6$, $R_7$, and $R_{10}$–$R_{13}$ are hydrogen. Among the latter embodiments, the invention provides a specific embodiment in which $X_1$–$X_3$ and $X_5$ are oxygen and $X_4$ is $NR_{17}$, m is 2, n is 0, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen. Also provided are embodiments in which $X_1$–$X_3$ and $X_5$ are oxygen and $X_4$ is $NR_{17}$, m is 2, n is 0, $R_{16}$ is dimethylamino, $R_{14}$ and $R_{15}$ independently are methyl or ethyl, and $R_3$, $R_4$, $R_6$, $R_7$, and $R_{10}$–$R_{13}$ are hydrogen or carboxyl; and, still more specifically, $X_1$–$X_3$ and $X_5$ are oxygen and $X_4$ is $NR_{17}$, m is 2, n is 0, $R_{16}$ is dimethylamino, $R_{14}$ and $R_{15}$ independently are methyl or ethyl, and $R_3$, $R_6$, $R_7$, and $R_{10}$–$R_{13}$ are hydrogen or carboxyl, and at least one of $R_{10}$–$R_{13}$ is carboxyl.

Particular examples of the above-described embodiments include the following compounds:

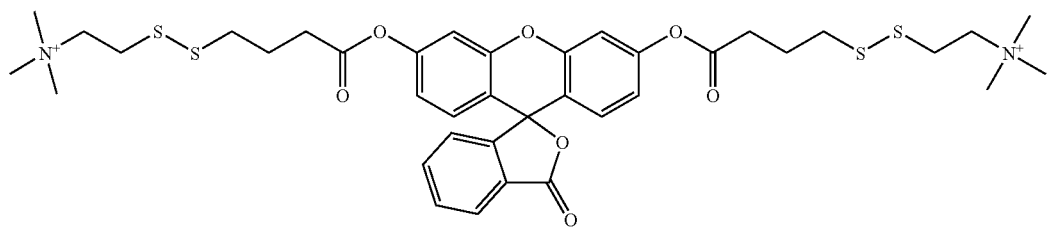

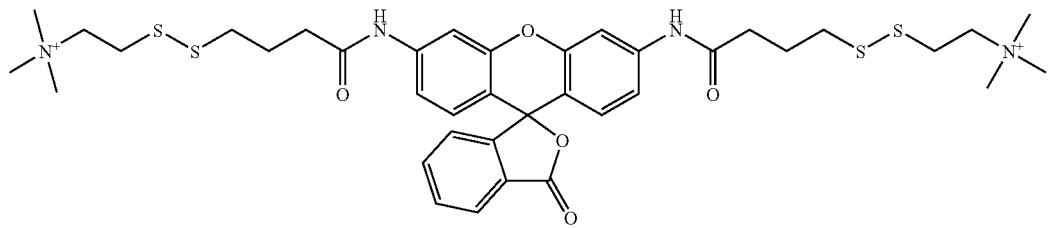

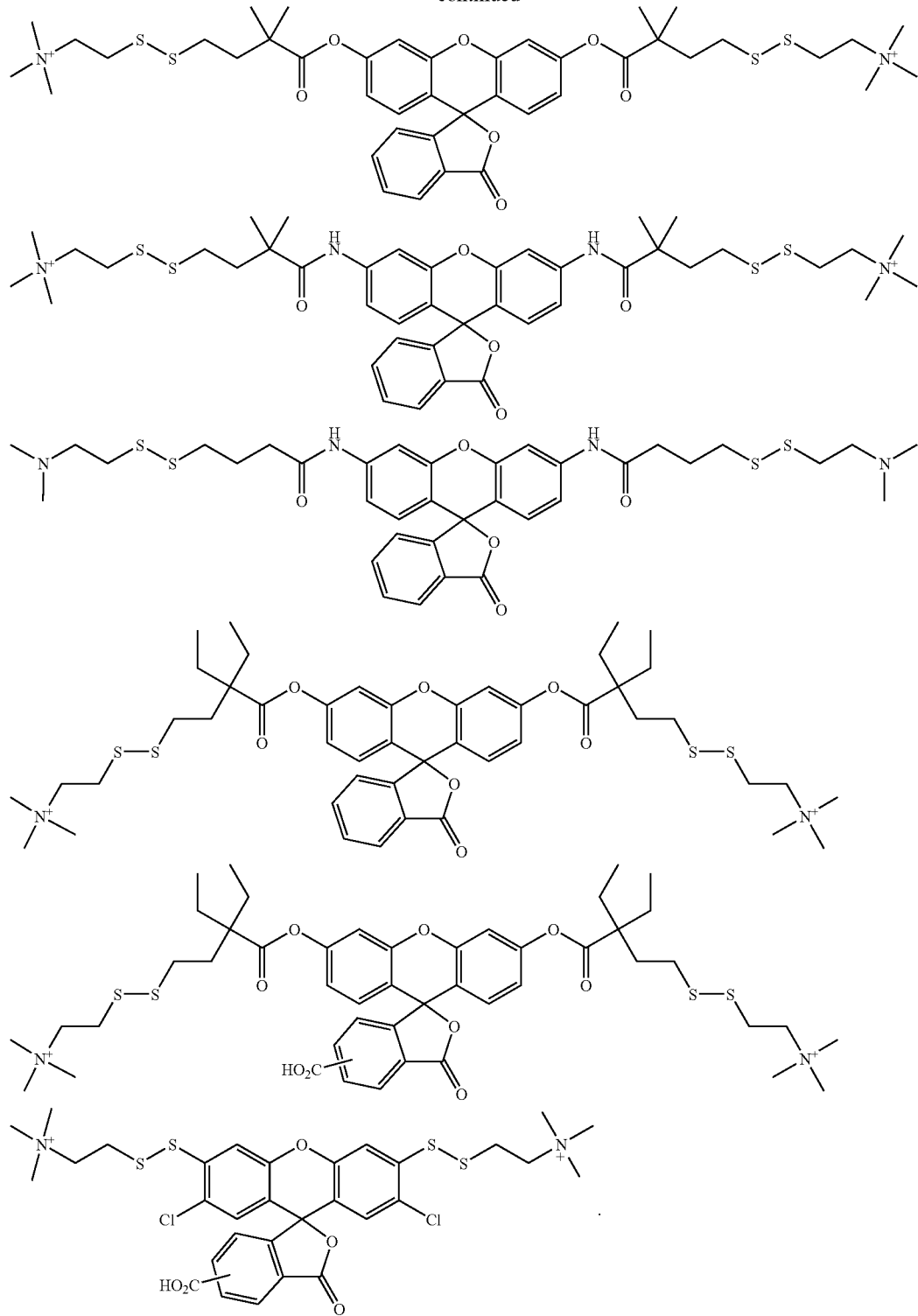
The compounds of the invention can be synthesized using procedures and materials known to those having skill in the organic chemistry synthesis arts, as shown generally in the Schemes below and illustrated in the Examples set forth in Sections 5.1–5.8. Scheme 1 below illustrates the general synthesis methodology for compounds for which $R_2$ and $R_8$ are:

Scheme 1
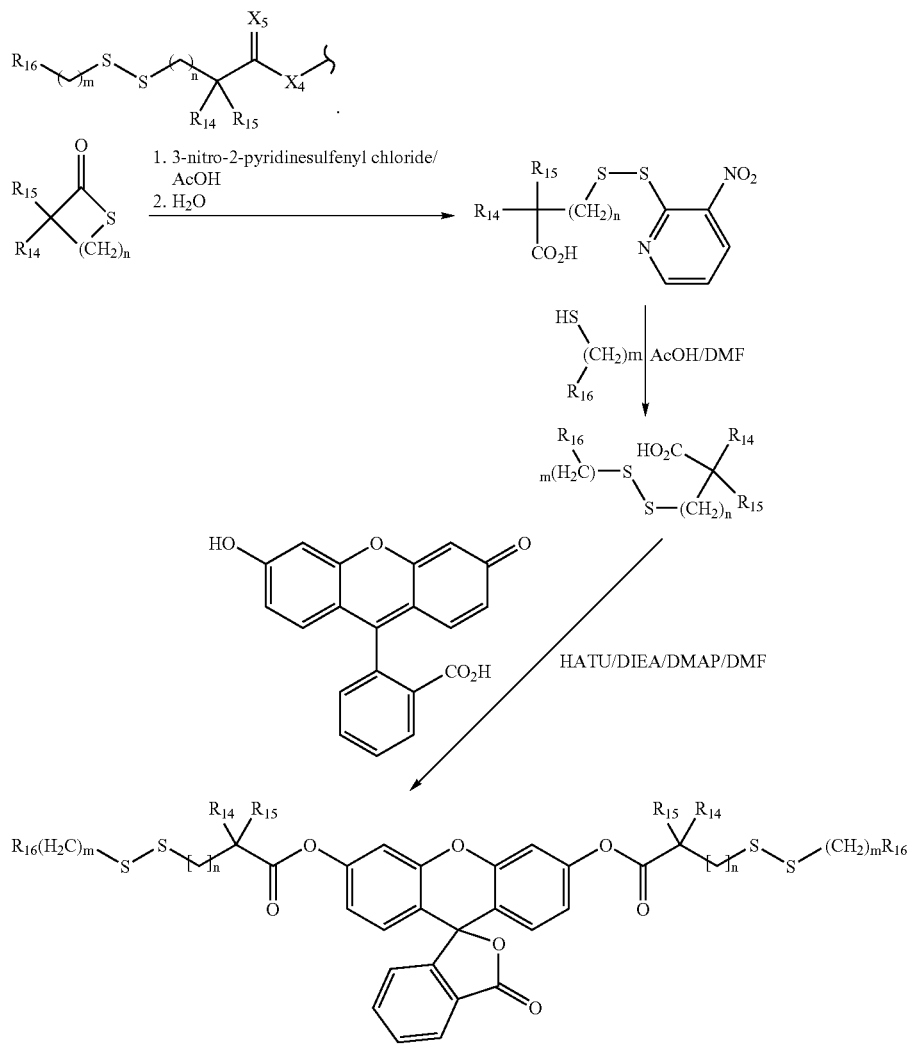
A general synthesis methodology is provided below (Scheme 2) for embodiments of the invention for which $R_2$ and $R_8$ are:
Scheme 2
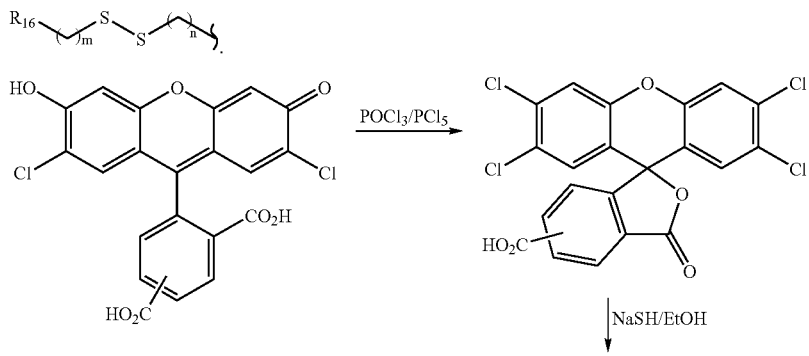

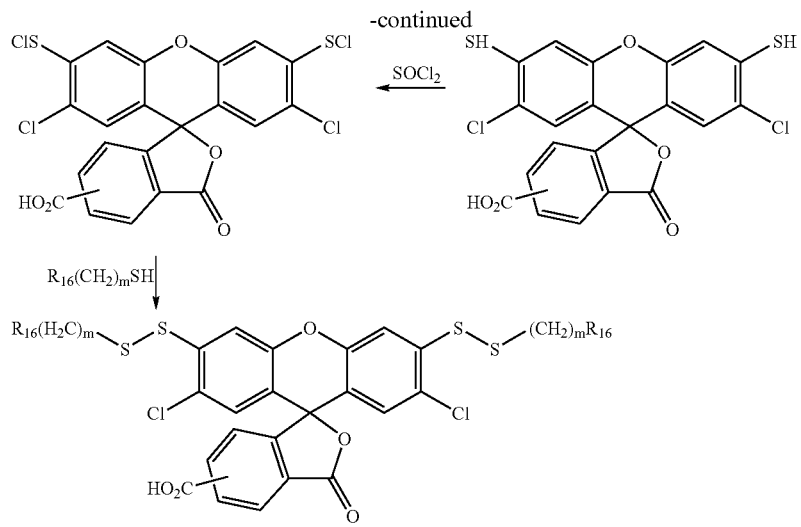

4.3 Detection and Quantitation of Cell Uptake

In another aspect, the compounds of the invention are useful as a reporters for detecting cell entry by specific compounds. More specifically, attachment of a compound of the invention to another molecule allows detection and quantitation of the transport of the molecule across a cell membrane. In one embodiment, the compound of the invention is attached to a molecule to be tested using a functional group contained on the fluorogenic compound of the invention, such as, but not limited to, a carboxylic acid group located on the lower aromatic ring of the fluorophore compound. Other appropriate functional groups that may be used in lieu of a carboxylic acid include by way of example amino, aminomethyl, halomethyl, haloacetamido, mercapto, maleimido, hydrazido, oxime, aldehyde, and keto. The choice of functional group will be familiar to those having skill in the organic synthesis and biochemistry arts. Compounds to be screened for their ability to facilitate cell entry by the fluorogenic or chromogenic reporter of the invention will include a functional group that is suitably reactive with the functional group on the fluorogenic or chromogenic reporter. Examples of compounds that can be screened for cell entry with a fluorophore according to the invention include, but are not limited to: peptides, peptoids, proteins, carbohydrates, nucleic acids, carbohydrates, small molecules and libraries containing such compounds, both random and non-random libraries.

Linker elements can also be used to facilitate attachment to the test molecule. In some instances it may be beneficial to also incorporate a cleavable linker, e.g., a disulfide or ester linkage between the reporter molecule and transporter group to allow the resultant fluorescent dye to exit the cell into the surrounding medium. Fluorescence is detected by fluorimetry or other methods, as appropriate. The choice of linker will be familiar to those having skill in the organic synthesis and biochemistry arts.

In one embodiment, the subject reporter is used to screen combinatorial peptoid libraries containing potential cell-transport molecules. Such libraries and methods for their synthesis are discussed in detail supra. In more specific embodiments, the fluorogenic or chromogenic reporter molecules of the invention are used to screen libraries by high-throughput screening methodologies to identify transport molecules that facilitate cell entry of biologically active molecules, e.g., enzyme agonists or antagonists, antibiotics, hormone agonists or antagonists, modulators of gene expression, and the like. The transport molecule can further include a "cargo" molecule that is to be transported by the peptoid into the intracellular milieu.

In one embodiment, diverse combinatorial libraries of peptoids are synthesized on a solid-phase resin, e.g., a resin bead, such that one compound is attached to each bead. The reporter of the invention is then conjugated to the peptoid compound on each bead. In some embodiments, the peptoids will further include a "cargo" molecule that is to be transported by the peptoid into the intracellular milieu. Examples of cargo molecules include, but are not limited to, antibiotic, enzyme agonists or antagonists, hormone analogs, cell growth promoting agents, cell growth inhibiting agents, anti-tumor agents, and apoptosis inducing agents. After attachment, the putative reporter-transport molecule is cleaved from the resin bead and is screened in a cell-based assay to determine whether cell entry is achieved (based on generation of fluorescence by the compound of the invention). Alternatively, the fluorogenic reporter of the invention can be attached to the putative transport molecule (e.g., the peptoid) in solution after cleavage from the resin bead.

The reporter system provide by the present invention is amenable to any cell that is to be screened for entry by desired compounds. Examples of such cells include by way of non-limiting example, prokaryotic cells, eukaryotic cells, mammalian cells, and plant cells. More specific examples of cell types include: fibroblasts, epithelial cells, neural cells, intestinal cells, embryonic and adult stem cells, ovarian cells, liver cells, prostate cells, kidney cells, bladder cells, blood cells, yeast cells, bacteria cells, and immune cells. Examples of human and non-human mammalian cell lines include, but are not limited to: HeLa, COS, CHO, BHK, Vero, SP2/0, DG44, HT1080, NIH3T3, THP-1, and NR833.

The reporter-transporter molecule conjugate according to the invention can be added to a cell culture, e.g., HeLa cell culture, and the fluorescence levels of the cell culture measured to identify whether the putative transporter compound facilitates cell entry (based on an increase in fluorescence). This may be accomplished by addition to microwell cell cultures, e.g., a 96- or 384-well format or on slides. Fluorescence will only be observed in cell cultures when the putative transport compound has entered the cells.

5 EXAMPLES

The following Examples are provided to illustrate certain aspects of the present invention and to aid those of skill in the art in practicing the invention. These Examples are in no way to be considered to limit the scope of the invention in any manner.

5.1 Synthesis of 3,3-Dimethyl-dihydro-thiophen-2-one

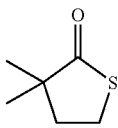

5

Potassium bis(trimethylsilyl)amide (4.62 g, 22 mmol) was added to 100 mL of anhydrous THF under argon ("Ar") with stirring. The reaction mixture was cooled to −78° C., and dihydro-thiophen-2-one (10 mmol, 0.87 mL) was added drop-wise followed by methyl iodide (40 mmol, 2.49 mL) and the reaction mixture was allowed to gradually warm to rt while stirring overnight. The solvent was removed by evaporation with a stream of $N_2$ and the residue was shaken with 5% aq. $Na_2S_2O_5$ and EtOAc. The aq. layer was separated and extracted with EtOAc (2×). The combined organic layers were washed with 1N $NaHSO_4$ and the aq. layer was separated and extracted with EtOAc (2×). The organic layers were recombined, dried over $MgSO_4$, filtered, and concentrated. Purification by silica gel chromatography (2.5% EtOAc in hexanes) gave the dimethylated dihydro-thiophen-2-one (370 mg, 28% yield). MH+=131.2.

5.2 3-Nitro-2-pyridinesulfenyl Chloride

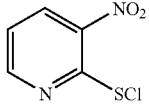

6

This compound was prepared according to a literature procedure: Pugh, et al. *Int. J. Peptide Prot. Res.* 1993, 42, 159. The overall yield was 71%.

5.3 4-(3'-nitro-2'-pyridinedithio)-2,2-dimethylbutyric Acid

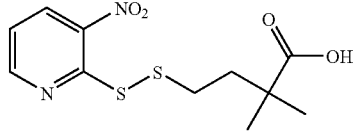

7

To thiobutyrolactone 5 (349 mg, 2.68 mmol) under Ar was added 12 mL acetic acid ("HOAc") followed by dropwise (16 mL/hr) addition of a HOAc solution (55 mL) containing sulfenyl chloride 6 (664 mg, 3.48 mmol). The solution was stirred overnight followed by addition of excess water and stirring for 1 h. The reaction mixture was concentrated, co-evaporated with MeOH (3×), resuspended in MeOH, and filtered (MeOH rinse). The MeOH filtrates were concentrated and purified by silica gel chromatography (1% MeOH/0.2% HOAc in $CH_2Cl_2$). The desired fractions were pooled, the solvent removed under vacuum, and the residue was co-evaporated with MeOH/MePh (3×) to afford the desired product 7 as a yellow solid (345 mg, 43% yield). MH+=303.4.

5.4 4-(2'-(trimethylamino)ethanedithio)-2,2-dimethylbutyric Acid

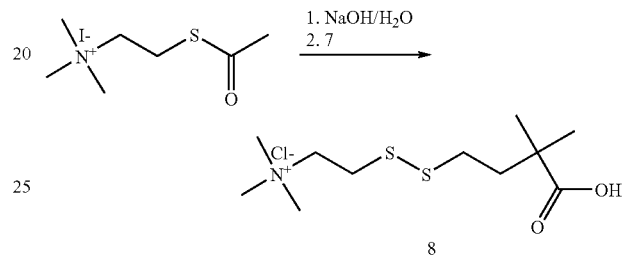

8

S-Acetylthiocholine iodide (100.5 g, 0.348 mol) was added to 1N NaOH (600 mL) that had been sparged with Ar. An additional 6N NaOH (102 mL) was added to adjust the pH to ~14. After stirring overnight the reaction was cooled in an ice bath and quenched by careful addition of conc. HCl (100 mL) under Ar. The solution was concentrated, co-evaporated with MeOH (3×), dried under high vacuum for several days to give the thiol product (152.4 g containing 2.28 mmol/g of thiocholine assuming 100% yield). To a AcOH (10 mL) solution of 7 (333 mg, 1.1 mmol) was added an AcOH solution (10 mL) of the crude thiocholine (1 g, 2.28 mmol) followed by 20 mL DMF rinse to complete the transfer. After stirring overnight the reaction was concentrated and co-evaporated initially with MeCN (caution: bumping) and then with MeOH. The residue was redissolved in MeCN/H₂O (20 mL), filtered, and purified by preparative scale HPLC (reverse phase C18 column; mobile phases: 0.1% TFA/H₂O and 0.1% TFA/MeCN). The desired fractions were lyophilized, then lyophilized 2× from 1.2N HCl and 1× from H₂O to give the desired product 8 (79 mg, 24% yield). M+=266.5.

5.5 Bis(4-(2'-(trimethylamino)ethanedithio)-2,2-dimethylbutyryl)carboxyfluorescein

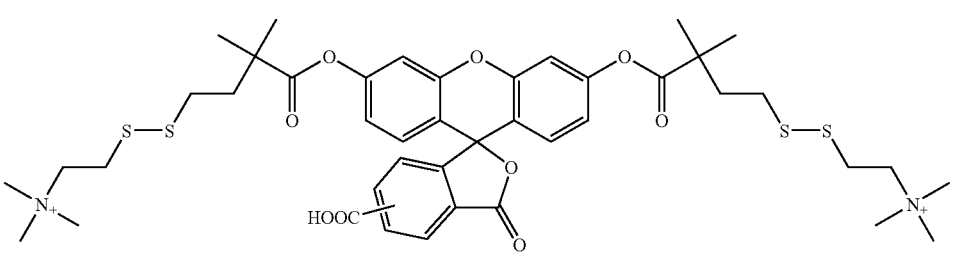

9

DMF (0.1 mL) was added to an oven dried flask containing acid 8 (4.5 mg, 15 μmol, 3 eq) and HATU (11.4 mg, 30 μmol, 6 eq) followed by addition of diisopropylethylamine (5.2 μL, 30 μmol, 6 eq). After stirring for 0.5 h, fluorescein (1.7 mg, 5 μmol, 1 eq) was added followed by 4-(dimethylamino)pyridine (1.8 mg, 15 μmol, 3 eq). Additional DMF (0.2 mL) was added after 1 h and the reaction was stirred overnight. A second reaction was carried out on the same scale as the first but in which the DMF was replaced with dimethylacetamide as the solvent. Both reactions were allowed to run for a few days (with continual addition of solvent) and then treated sequentially with 0.1% TFA (0.5 mL) followed by neat TFA (0.02 mL). The crude mixtures were combined, solubilized in DMF, filtered, and purified by prep HPLC (reverse phase C18 column; mobile phases: 0.1% TFA/H$_2$O and 0.1% TFA/MeCN) to give the desired product 9 (2.4 mg, 23% yield). (M/2)$^{2+}$=414.5.

5.6 5(6)-Carboxy-2',3',6',7'-tetrachlorofluorescein

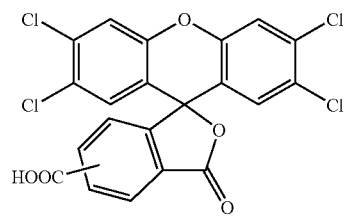

10

To 5(6)-carboxy-2',7'-dichlorofluorescein (50 mg, 112 μmol) was added POCl$_3$ (5 mL) and PCl$_5$ (500 mg) with stirring. The reaction mixture was heated to 115° C. for 1 hr., then allowed to cool to room temperature. The solvent was removed under vacuum, and the residue was co-evaporated three times with CH$_2$Cl$_2$. To the residue was added water with stirring at 0° C. The mixture was filtered; then the solid washed with water and air-dried. The solid was co-evaporated two times from cyanonitrile (CH$_3$CN) to yield 52 mg (96%) of the title compound as a white solid. The identity of the product was verified by electrospray MS (MH$^+$=483).

5.7 5(6)-Carboxy-2',7'-dichloro-3',6'-dithiofluorescein

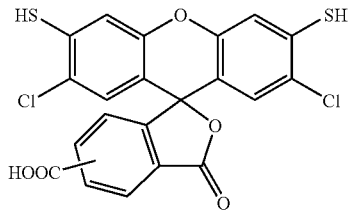

11

To compound 10 (52 mg, 108 μmol) was added 5 mL EtOH and NaSH.xH$_2$O (235 mg, 1.08 mmol) with stirring, and the mixture was heated to reflux for 90 min. The reaction mixture was allowed to cool to room temperature, and the solvent was evaporated with a stream of nitrogen. To the residue was added 0.1 N hydrochloric acid (HCl) containing 5% Na$_2$S$_2$O$_5$ with stirring, and the mixture was filtered. The solid was washed with 0.1 N HCl, and air dried to afford the title compound as a beige solid. The identity of the product was verified by electrospray MS (MH$^+$=477/479)

5.8 5(6)-Carboxy-2',7'-dichloro-3',6'-bis(2'''-trimethylammonium(ethanedithio))fluorescein

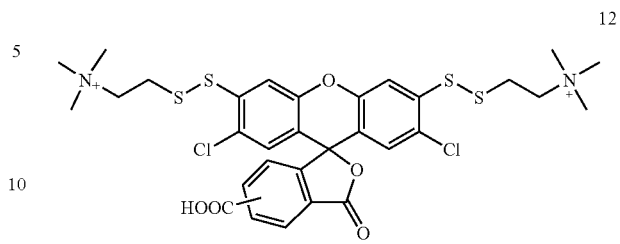

12

Compound 11 was dissolved in SO$_2$Cl$_2$ (4 mL) and CH$_2$Cl$_2$ (4 mL) with stirring and heated to reflux for 1 hr. The reaction was cooled to room temperature, the solvent was removed under vacuum, and the residue was co-evaporated three times with CH$_2$Cl$_2$. The residue was dissolved in 5 mL AcOH, and thiocholine (trifluoroacetic acid salt, 111 mg, 477 μmol) was added with stirring, and the mixture was heated to reflux for 2 hr. The reaction mixture was cooled to room temperature, then purified by reverse-phase HPLC to afford the title compound. The identity of the product was verified by electrospray MS (M/2$^{2+}$=357).

5.9 Demonstration That Reporter According to the Invention is Selectively Fluorescent Under Reducing Conditions An experiment was conducted to determine the effect of reducing conditions versus non-reducing conditions on a reporter compound according to the invention (compound 9). Two incubations were conducted with compound 9 at a concentration of 50 mM. A control incubation was conducted which compared the same molar concentration of compound 9 in 10 mM Na phosphate at pH 7.5. A reducing reaction composition was made comprising the same buffer, and 10 mM dithiothreitol (DTT). After one minute of incubation at room temperature, strong green fluorescence was measured. Consistent with these fluorescence results, mass spectrometry analysis revealed that the control reaction contained only compound 9, and that the DTT containing reaction composition contained only fluorescein. For this example, synthesis. of compound was conducted as previously described.

5.10 Fluorescence of Compound 9 overtime, pH 7.5, 37° C.

FIG. 1 contains the fluorescence (excitation 485 nm, emission 535 nm) of compound 9 over time under various conditions. For the conditions labeled "optimem" (solid red circle), compound 9 was incubated in Optimem (Gibco BRL), a reduced serum cell culture medium. For the conditions labeled "cell lysate" (solid green square), compound 9 was incubated in a HeLa cell lysate prepared from approximately 2×10$^6$ cells lysed by freeze/thaw in a buffer containing 20 mM Tris-HCl, 137 mM NaCl, 1% Triton, and 15% glycerol in a volume of 100 μL. For the conditions labeled "buffer+salt" (solid brown triangle) compound 9 was incubated in 10 mM Na phosphate containing 154 mM NaCl, and for the conditions labeled "10 mM β-ME" (solid orange diamond), compound 9 was incubated in 10 mM Na phosphate containing 154 mM NaCl and 10 mM β-mercaptoethanol. The concentration of compound 9 was 50 μM in each case, diluted from a 2 mM stock solution in DMF. All experiments were carried out at 37° C., and at a pH of 7.5, except "cell lysate" for which the pH was approximateLy 7.8. The total volume of each incubation was 100 μL.

Results are expressed as a percentage of the fluorescence of a fluorescein control at the same concentration under the same conditions.

5.11 Fluorescence of 9 and Unsubstituted Analog Over Time, pH 7.5, 37° C.

Figure 2:
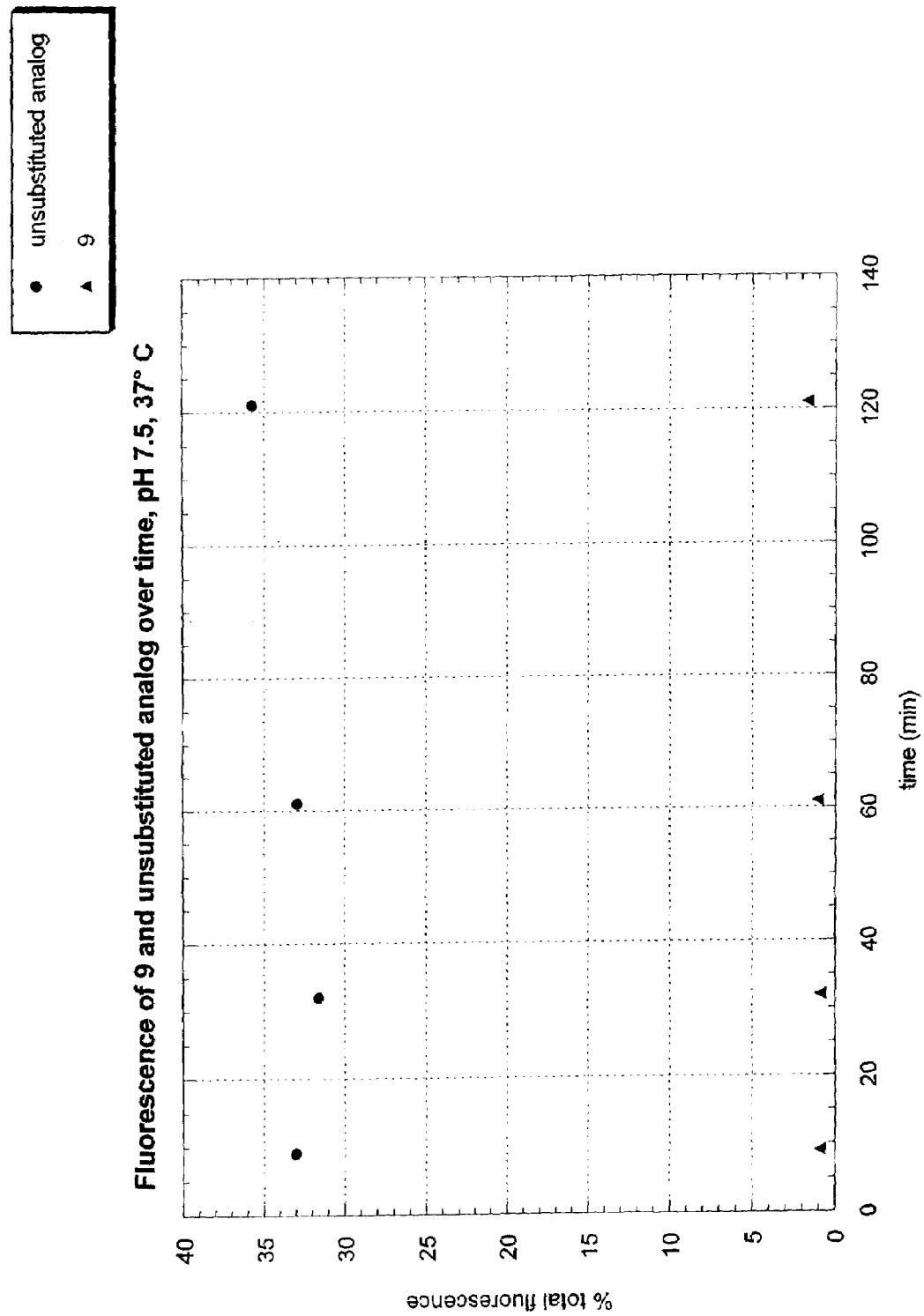
FIG. 2 shows the fluorescence of compound 9 and an unsubstituted analog over time at pH 7.5, 37° C.

FIG. 2 shows the fluorescence (excitation 485 nm, emission 535 nm) over time of compound 9 and an analog in which the α,α-dimethyl substituents on the acyl groups have been replaced by α,α-dihydrogen substituents. Each compound was incubated at a concentration of 50 μM (diluted from a 2 mM stock in DMF) in 10 mM Na phosphate, pH 7.5, containing 154 mM NaCl, at 37° C. The volume of each incubation was 100 μL. Results are expressed as a percentage of the fluorescence of a fluorescein control at the same concentration under the same conditions.

5.12 Fluorescence of 9 at 60 min. vs. [β-ME] (pH 7.5, 37° C.)

FIG. 3 shows the fluorescence (excitation 485 nm, emission 535 nm) of compound 9 after a 60-minute incubation in 10 mM Na phosphate, pH 7.5, containing 154 mM NaCl and β-mercaptoethanol at concentrations of 0.1, 1, 10, and 100 mM. The volume of each incubation was 100 μL, and the temperature was 37° C. Results are expressed as a percentage of the fluorescence of a fluorescein control at the same concentration under the same conditions.

5.13 Fluorescence of 12

An experiment was conducted to test the ability of compound 12 to respond to reducing conditions. Two incubations were performed: in the first, a control incubation, a sample of compound 12 was added to pH 7.5 buffer. In a second incubation (+DTT), the same amount of compound 12 was added to pH 7.5 buffer and then DTT was added to a final concentration of 10 mM. Within one minute after addition of DTT to the second incubation, the solution turned light blue, indicating the formation of the free dichlorodithiofluorescein dye. The control incubation remained colorless.

We claim:

1. A method for determining whether a compound is a transport molecule that is internalized by a cell comprising:
   a. contacting a cell with a conjugate comprising a potential transport compound and a reporter compound selected from the group consisting of:

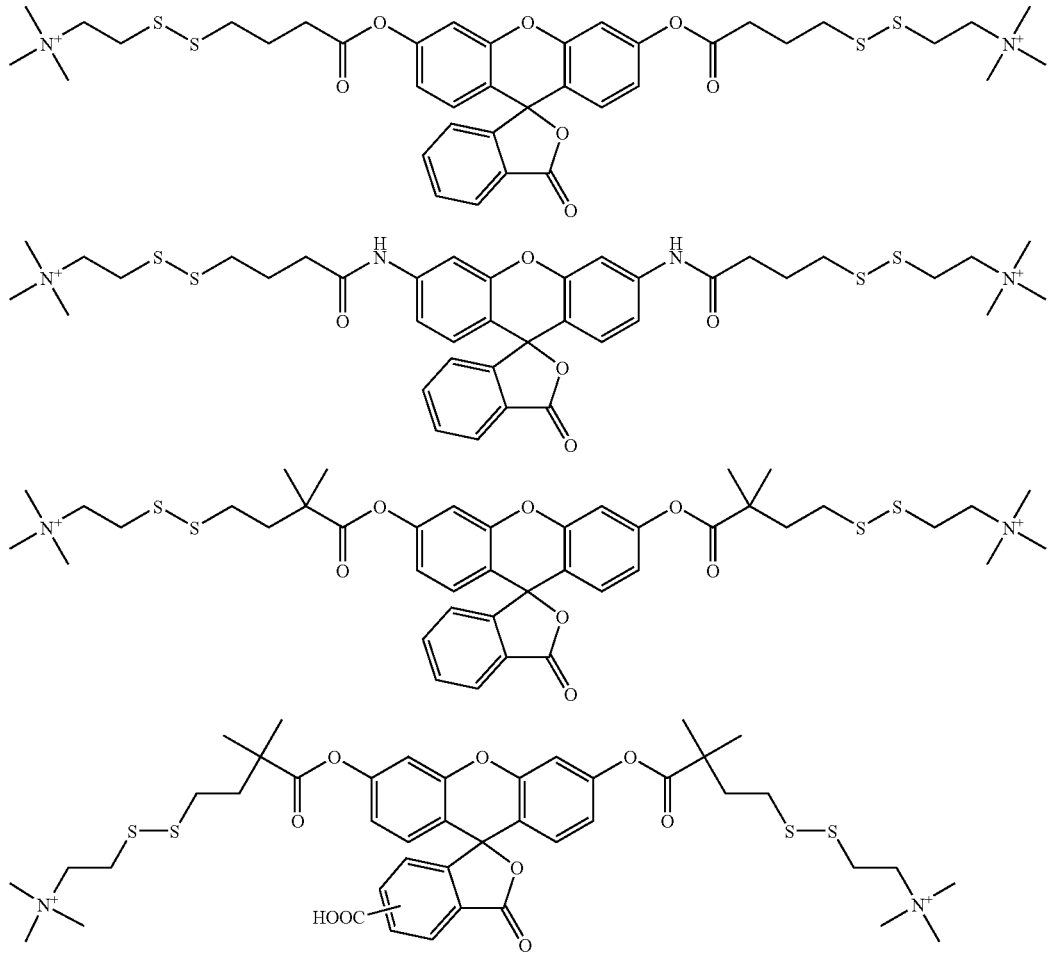

-continued
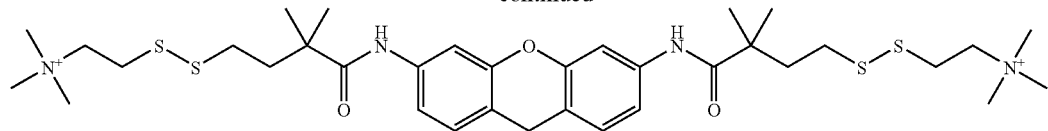
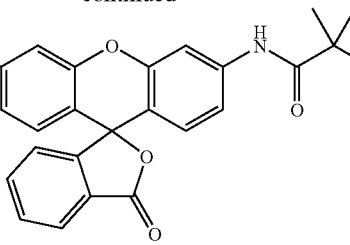
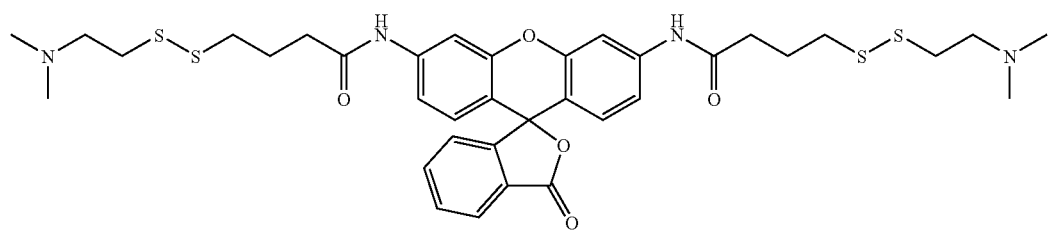
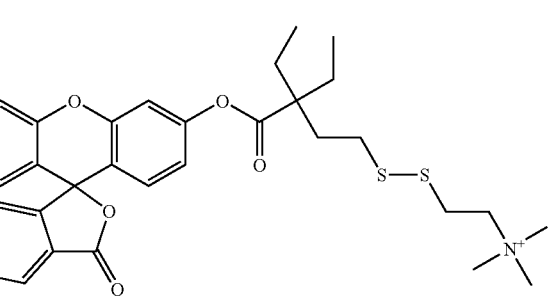
and
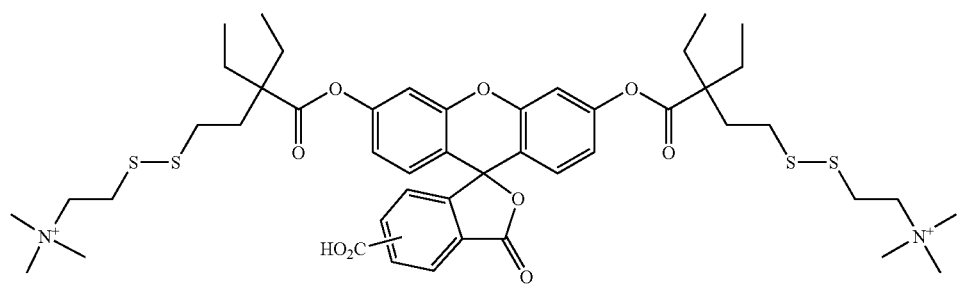
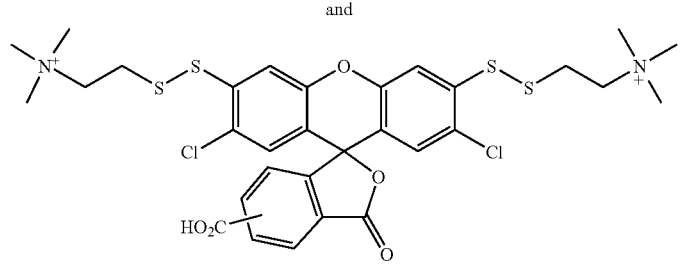
b. detecting whether fluorescence is generated after said contacting step; and
c. correlating to generation of fluorescence to the internalization of the transport compound by the cell.

2. The method of claim 1, wherein the reporter compound is:

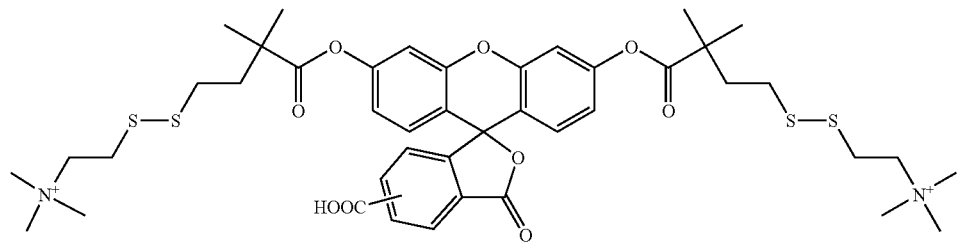

3. The method of claim 1, wherein the reporter compound is:

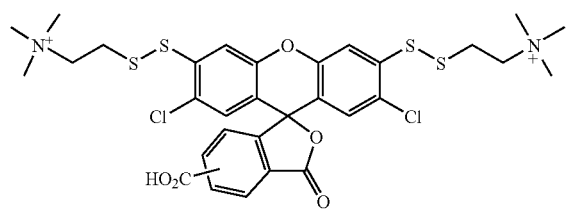

4. The method of claim 1 wherein the potential transport compound is attached to a solid phase by a cleavable linkage and is cleaved therefrom prior to contacting with the cell.

5. The method of claim 4 wherein the solid phase is a resinous bead.

6. The method of claim 1 wherein the potential transport compound is selected from the group consisting of a peptide, protein, nucleic acid, peptoid, carbohydrate, and a steroid.

7. The method of claim 1 wherein the potential transport compound is contained in a combinatorial chemical library.

8. The method of claim 7 wherein the combinatorial chemical library is a peptoid library.

9. The method of claim 1 wherein, prior to contacting the cell, the reporter is chemically attached to the potential transport compound while the compound and reporter are in solution.

10. The method of claim 1 wherein, prior to contacting the cell, the reporter is chemically attached to the potential transport compound while such compound is attached to a solid phase.

11. The method of claim 1, wherein the conjugate is contained within a conjugate library, and the transport capability of the compounds of the conjugates in the library is determined by performing steps (a) through (c) for the conjugates of the library.

12. The method of claim 1 wherein the cell is in a cell culture.

13. The method of claim 12 wherein the cell culture is in a microwell or on a covered slide.

14. The method of claim 1 wherein the fluorescence is detected by direct imaging.

15. The method of claim 1 wherein the fluorescence is detected by flow cytometry.

16. The method of claim 1 wherein the conjugate further comprises a cargo molecule.

17. The method of claim 16 wherein the cargo molecule is an active agent.

18. The method of claim 17 wherein said active agent is an antibiotic, enzyme inhibitor, hormone agonist or antagonist, or cell growth modulator.

19. The method of claim 18 wherein the active agent is an antibiotic.

* * * * *